(12) United States Patent
Yachie et al.

(10) Patent No.: US 11,545,182 B2
(45) Date of Patent: Jan. 3, 2023

(54) ENCRYPTION METHOD, DECRYPTION METHOD, ENCRYPTION SYSTEM AND DECRYPTION SYSTEM

(71) Applicant: The System Biology Institute, Tokyo (JP)

(72) Inventors: Nozomu Yachie, Tokyo (JP); Junichi Sugahara, Tsuruoka (JP)

(73) Assignee: The Systems Biology Institute, Tokyo (JP)

( * ) Notice: Subject to any disclaimer, the term of this patent is extended or adjusted under 35 U.S.C. 154(b) by 319 days.

(21) Appl. No.: 16/650,013

(22) PCT Filed: Sep. 28, 2018

(86) PCT No.: PCT/JP2018/036384
§ 371 (c)(1),
(2) Date: Mar. 24, 2020

(87) PCT Pub. No.: WO2019/066007
PCT Pub. Date: Apr. 4, 2019

(65) Prior Publication Data
US 2020/0279583 A1    Sep. 3, 2020

(30) Foreign Application Priority Data

Sep. 29, 2017    (JP) .............................. JP2017-191076

(51) Int. Cl.
*G11B 20/00*    (2006.01)
*G06F 21/10*    (2013.01)
(Continued)

(52) U.S. Cl.
CPC .......... *G11B 20/0021* (2013.01); *G06F 21/10* (2013.01); *H04L 9/08* (2013.01);
(Continued)

(58) Field of Classification Search
CPC ................. G11B 20/0021; G06F 21/10; G06F 2221/2107; G06F 21/602; H04L 9/08;
(Continued)

(56) References Cited

U.S. PATENT DOCUMENTS

2009/0110192 A1    4/2009    Elrod et al.
2010/0046811 A1*   2/2010    Harris .................... G06K 9/00
                                                        382/115
(Continued)

FOREIGN PATENT DOCUMENTS

JP    S63-248394 A    10/1988
JP    H07-327029 A    12/1995
(Continued)

OTHER PUBLICATIONS

International Search Report issued in corresponding International Patent Application No. PCT/JP2018/036384 dated Dec. 18, 2018.
(Continued)

*Primary Examiner* — Mohammad W Reza
(74) *Attorney, Agent, or Firm* — Morgan, Lewis & Bockius LLP

(57) ABSTRACT

An encryption method includes an operation method of an encryption system and is a method of encrypting encryption target information.

13 Claims, 12 Drawing Sheets

Specification includes a Sequence Listing.

(51) Int. Cl.
  *H04L 9/08* (2006.01)
  *H04N 7/167* (2011.01)
(52) U.S. Cl.
  CPC ... *H04N 7/1675* (2013.01); *G06F 2221/2107* (2013.01); *H04L 2209/60* (2013.01)
(58) Field of Classification Search
  CPC . H04L 2209/60; H04L 9/0625; H04L 9/0863; H04N 7/1675; C12N 15/09; C12Q 1/68; G09C 1/00
  See application file for complete search history.

(56) References Cited

U.S. PATENT DOCUMENTS

| | | | | |
|---|---|---|---|---|
| 2013/0266135 | A1* | 10/2013 | Pratt | C12Q 1/68 380/28 |
| 2017/0005794 | A1* | 1/2017 | Paddon | H04L 9/0866 |

FOREIGN PATENT DOCUMENTS

| | | | |
|---|---|---|---|
| JP | 2000-315999 A | 11/2000 | |
| JP | 2002-288605 A | 10/2002 | |
| JP | 2016-075765 A | 5/2016 | |
| WO | WO-2013067542 A1 * | 5/2013 | ......... G01N 33/6803 |

OTHER PUBLICATIONS

International Preliminary Report on Patentability and Written Opinion issued in corresponding International Patent Application No. PCT/JP2018/036384 dated Apr. 9, 2020.

Yachie et al., "Alignment-Based Approach for Durable Data Storage into Living Organisms," Biotechnology Programs, 23: 501-505 (2007).

Yachie et al., "Pooled-matrix protein interaction screens using Barcode Fusion Genetics," Molecular Systems Biology, 12: 863 (2016).

\* cited by examiner

ENCRYPTION METHOD, DECRYPTION METHOD, ENCRYPTION SYSTEM AND DECRYPTION SYSTEM

TECHNICAL FIELD

The present invention relates to an encryption method, a decryption method, an encryption system and a decryption system.

BACKGROUND ART

An encryption algorithm and keys are used in order to convert information (plaintext) that is understood into information (ciphertext) that is not understood. Encryption in which common keys are used during encryption and during decryption in which ciphertext is returned to information that is understood is known as "common key encryption" (for example, refer to Patent Literature 1). Encryption in which different keys are used during encryption and during decryption is known as "public key encryption." As an encryption algorithm used, 2-key triple DES, RC4, and the like are used in the common key encryption, and RSA and hash functions such as SHA-1 and SHA-2 are used in the public key encryption.

CITATION LIST

Patent Literature

[Patent Literature 1] Japanese Unexamined Patent Publication No. 2016-75765

SUMMARY OF INVENTION

Technical Problem

The security of the above encryption algorithm is guaranteed only in Neumann type computers, which are almost all calculators in modern society, but is not guaranteed in non-Neumann type computers. For example, unidirectionality of public key generation, encryption by a public key, and decryption by a private key on which the security of RSA is based, is based on the fact that a product of two large prime numbers p and q can be easily calculated in a Neumann type computer but prime factorization of pq is difficult. It is logically known that a quantum computer and the like can perform prime factorization at a high speed (Shor's theorem), and security is not guaranteed if a quantum computer is assumed.

Accordingly, it is considered that it is difficult to secure security with these encryption algorithms due to increases in cost performance of computers and progress of encryption and decryption technology in the future. Under these circumstances, the National Institute of Standards and Technology (NIST) announced that encryption algorithms such as 2-key triple DES, RSA and SHA-1 which are currently mainstream, will not be used in the US Federal Agency System after 2011, in various guidelines. In addition, in February 2017, Google in the USA released two PDFs having the same hash value using SHA-1, and pointed out the risk of SHA-1. Under the above circumstances, a more secure encryption system is required.

The present invention has been made in view of the above circumstances, and an object of the present invention is to provide an encryption method, a decryption method, an encryption system and a decryption system through which more secure encryption is possible.

Solution to Problem

In order to achieve the above object, an encryption method according to one embodiment of the present invention is an encryption method including an operation method of an encryption system for encrypting encryption target information, the method including: a key information reading step in which key information of each compound of one set included in a key medium set including a plurality of sets including two or more compounds which are physically associated with each other in which different key information items are recorded is read; an encryption step in which the encryption system encrypts encryption target information using one or more of the key information items read in the key information reading step and generates encrypted information; and a transmission step in which the encryption system transmits the encrypted information generated in the encryption step and an ID based on one or more of the key information items read in the key information reading step to a decryption system.

In order to achieve the above object, a decryption method according to one embodiment of the present invention is a decryption method which is an operation method of a decryption system for decrypting encrypted information encrypted by the encryption method according to one embodiment of the present invention, wherein the decryption system includes a storage means configured to store an ID corresponding to each set included in the key medium set and decryption information in association, wherein the decryption method includes a reception step in which the encrypted information and ID are received from the encryption system; a decryption information acquisition step in which decryption information stored in the storage means, which corresponds to the ID received in the reception step is acquired; and a decryption step in which the encrypted information received in the reception step is decrypted using the decryption information acquired in the decryption information acquisition step.

In the encryption method according to one embodiment of the present invention, from the plurality (for example, tens of thousands) of sets contained in the key medium set, key information for each compound of one set including a plurality of key information items including compounds which are physically associated with each other in which different key information items are recorded is read and used for encryption. Therefore, it is difficult for a third party to identify a set used for encryption among the plurality of sets, and in order to decrypt key information, it is necessary to release the physically associated relationship. Therefore, it is difficult for a third party to identify key information. Therefore, more secure encryption can be performed.

In addition, during decryption, decryption is performed using decryption information stored in correspondence to the received ID. Therefore, it is possible to reliably decrypt the encrypted information encrypted by the above encryption method.

The compound may be a compound selected from the group consisting of low molecules, synthetic polymer and biopolymers. In such a configuration, it is possible to reliably make it difficult to identify key information, and it is possible to reliably perform more secure encryption.

The compound may be a nucleic acid, and the key information may be a base sequence of the nucleic acid. In such a configuration, it is possible to read key information easily and reliably, and as a result, one embodiment of the present invention can be implemented easily and reliably.

The set may be associated by cells or capsules containing the compound or a circular DNA chain. In such a configuration, it is possible to easily and reliably generate a set including a plurality of key information items including compounds which are included in the key medium set and physically associated with each other in which different key information items are recorded, and as a result, one embodiment of the present invention can be implemented easily and reliably.

Here, the present invention can be described as inventions of an encryption method and a decryption method as described above and can also be described as inventions of an encryption system and a decryption system as will be described below.

That is, an encryption system according to one embodiment of the present invention is an encryption system that encrypts encryption target information, the system including a key information reading means configured to read key information of each compound of one set included in a key medium set including a plurality of sets including two or more compounds which are physically associated with each other in which different key information items are recorded; an encryption means configured to encrypt encryption target information using one or more of the key information items read by the key information reading means and generate encrypted information; and a transmission means configured to transmit the encrypted information generated by the encryption means and an ID based on one or more of the key information items read by the key information reading means to a decryption system.

In addition, a decryption system according to one embodiment of the present invention is a decryption system which decrypts the encrypted information encrypted by the encryption system according to one embodiment of the present invention, the system including a storage means configured to store an ID corresponding to each set included in the key medium set and decryption information in association; a reception means configured to receive the encrypted information and ID from the encryption system; a decryption information acquisition means configured to acquire decryption information stored in the storage means, which corresponds to the ID received by the reception means; and a decryption means configured to decrypt the encrypted information received by the reception means using the decryption information acquired by the decryption information acquisition means.

Advantageous Effects of Invention

According to one embodiment of the present invention, since it is difficult for a third party to identify key information used for encryption, more secure encryption can be performed.

DESCRIPTION OF EMBODIMENTS

Figure 1:
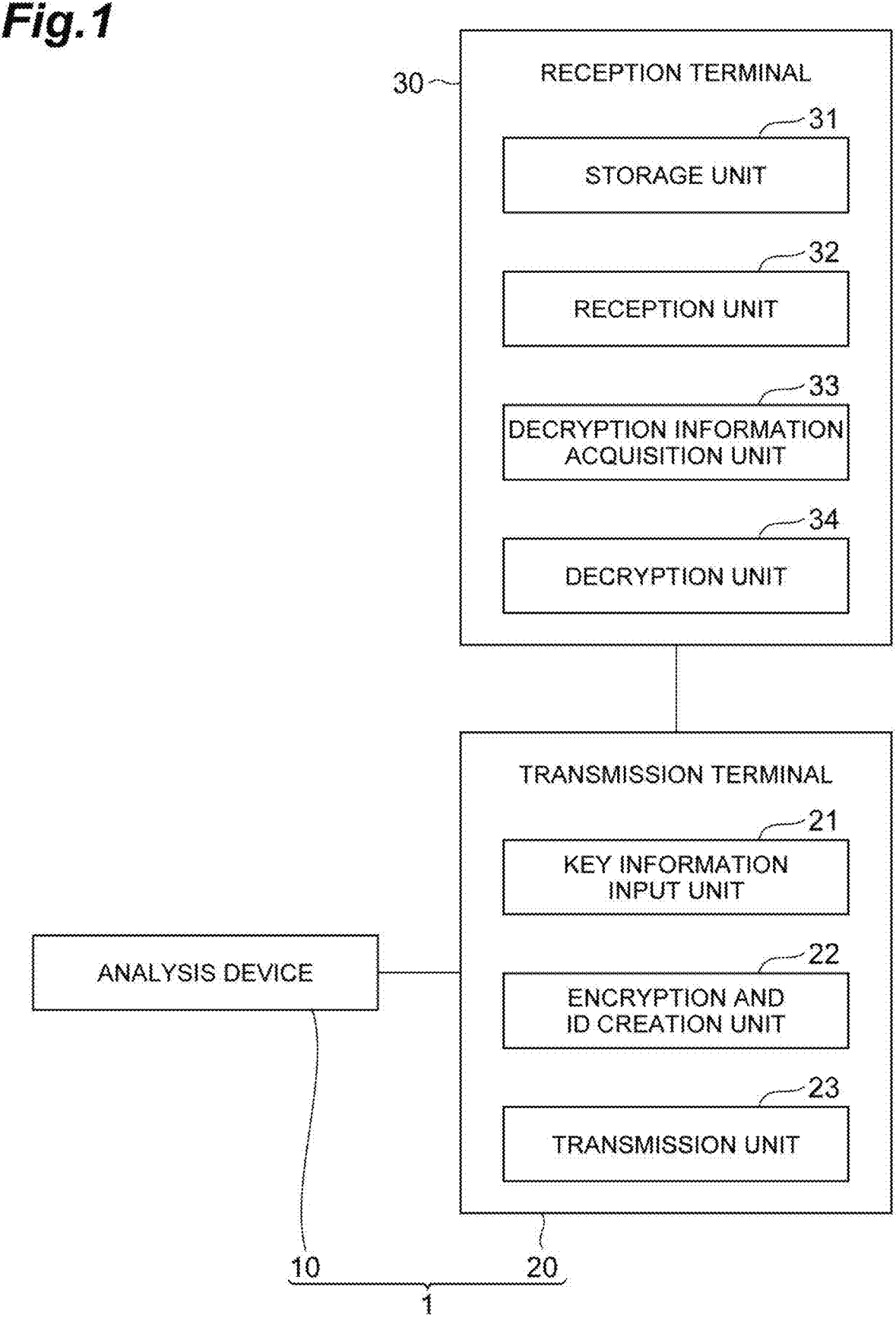
FIG. 1 is a diagram showing a configuration of an encryption system and a decryption system according to an embodiment of the present invention.

Hereinafter, an encryption method, a decryption method, an encryption system and a decryption system according to embodiments of the present invention will be described in detail with reference to the drawings. Here, in description of the drawings, the same components will be denoted with the same reference numerals and redundant descriptions will be omitted.

FIG. 1 shows an encryption system 1 according to the present embodiment. The encryption system 1 includes an analysis device 10 and a transmission terminal 20. In addition, FIG. 1 shows a reception terminal 30 which is a decryption system according to the present embodiment. The encryption system 1 and the reception terminal 30 according to the present embodiment are used in a system that encrypts plaintext, which is information that is understood, and transmits and receives it. The encryption system 1 is used by an information transmitter (information provider) that encrypts plaintext and transmits (provides) it. The reception terminal 30 is used by an information recipient that receives the encrypted plaintext.

A physical key medium set is used for encryption in the present embodiment. As will be described below, the key medium set is generally provided from the information recipient to the information transmitter. The key medium set includes a set (unit) including two or more compounds. Hereinafter, the set will be referred to as a container. In the present embodiment, the number of compounds contained in one container may be 2 (2 types), 3 (3 types), or 4 (4 types). In addition, 5 or more compounds may be contained in one container. When the number (type) of compounds (keys) is larger, confidentiality becomes higher. However, a time for adjustment becomes longer.

The key medium set includes, for example, at least 50,000 containers. Here, the number of containers contained in the key medium set may be 50,000 or more, 100,000 or more, 1,000,000 or more, or 2,000,000 or more. When the number of containers contained in the key medium set is larger, confidentiality becomes higher. However, a time for adjustment becomes longer. The number of compounds contained in one container and the number of containers contained in the key medium set may be determined according to the degree of confidentiality.

Compounds constituting the container are present in a state in which they are spatially constrained so that they are not separated. That is, compounds constituting the container are physically associated with each other due to a limited space or by a means such as linking. In addition, in each of compounds constituting the container, different key information is recorded. The key information is information used for encryption and decryption of plaintext.

A compound according to an embodiment of the present embodiment is DNA which is a biopolymer. When DNA is used as a compound, a base sequence is used as key information. Hereinafter, the compound is called a DNA barcode. Here, nucleic acids other than DNA, for example, RNA or artificial nucleic acids such as a locked nucleic acid (LNA), a bridged nucleic acid (BNA), and a spherical nucleic acid (SNA), may be used. Details of the key medium set will be described below.

Next, the analysis device 10, the transmission terminal 20, and the reception terminal 30 according to the present embodiment will be described.

The analysis device 10 is a key information reading means configured to read key information of nucleic acids of one container contained in the key medium set, that is, base sequences. Examples of the analysis device 10 include a DNA sequencer. The analysis device 10 is connected to the transmission terminal 20, and outputs the base sequences of nucleic acids obtained by analysis to the transmission terminal 20.

The transmission terminal 20 is a device that encrypts plaintext which is encryption target information and transmits the encrypted plaintext to the reception terminal 30. The reception terminal 30 is a device that receives and decrypts ciphertext which is plaintext encrypted by the transmission terminal 20. The transmission terminal 20 and the reception terminal 30 are, specifically, for example, a computer (for example, a personal computer (PC)) including hardware such as a central processing unit (CPU), a memory, and a communication module. Functions of the transmission terminal 20 and the reception terminal 30, which will be described below, are exhibited when these components are operated by a program or the like. The transmission terminal 20 and the reception terminal 30 can transmit and receive information to and from each other via a communication network such as the Internet.

Next, functions of the transmission terminal 20 and the reception terminal 30 according to the present embodiment will be described. As shown in FIG. 1, the transmission terminal 20 includes a key information input unit 21, an encryption and ID creation unit 22, and a transmission unit 23.

The key information input unit 21 inputs base sequences which are key information of nucleic acids of one container from the analysis device 10. The key information input unit 21 converts into input bit data (bit information) based on a preset conversion rule. For example, in the base sequence, A is replaced with 00, G is replaced with 01, C is replaced with 10, and T is replaced with 10. In the transmission terminal 20, thereafter, key information converted into bit data is used. By performing conversion into bit data, information that is not limited to expression of AGCT can be used as key information. However, the base sequence itself may be used as key information without performing conversion into bit data. The key information input unit 21 outputs key information to the encryption and ID creation unit 22. Here, the input of the base sequence to the transmission terminal 20 does not necessarily need to be directly performed from the analysis device 10, and may be performed by an operation of the information transmitter (for example, an operation using a recording medium).

The encryption and ID creation unit 22 is an encryption means Configured to encrypt plaintext which is encryption target information using one or more of the key information items input from the key information input unit 21 and generate ciphertext which is encrypted information. The encryption in the present embodiment may be based on common key encryption. The plaintext which is encryption target information is input to the transmission terminal 20 in advance by an operation of the information transmitter or the like.

The encryption and ID creation unit 22 inputs all key information items from the key information input unit 21. The encryption and ID creation unit 22 selects one or more of input key information items as information used for encryption. A selection method is a method that is determined in advance by the information transmitter. For example, the encryption and ID creation unit 22 selects any one of input key information items as information used for encryption. The encryption and ID creation unit 22 encrypts plaintext using a preset and stored encryption algorithm and generates ciphertext using the selected key information as a common key. The preset and stored encryption algorithm is, for example, an algorithm that is determined in advance by the information recipient, and 2-key triple DES or the like is used.

The encryption algorithm can be different for each information transmitter, and thus confidentiality can be further improved. In addition, the encryption and ID creation unit 22 may perform encryption using all of input key information items as a common key. For example, a key obtained by sequentially connecting the input key information items may be used as a common key. Alternatively, in the case of encryption using 2-key triple DES, each may be used as a common key.

In addition, the encryption and ID creation unit 22 is a means configured to create an ID from the input key information. The ID is information used to identify decryption information used for decryption in the reception terminal 30. For example, the encryption and ID creation unit 22 selects any one among key information items that have not been used as information for encryption and uses it as an ID. Since the information recipient knows all of a plurality of key information items which are physically associated with each other, it can identify all of a plurality of key information items which are physically associated with each other with only one key information item. However, when the information recipient issues an instruction to create an ID from one or more key information items, the instruction is followed. The key information used for encryption and the key information used for an ID are never the same. The key information used as an ID may be used without change or a result obtained by encrypting the key information according to an instruction from the information recipient may be used as an ID. As described above, the encryption and ID creation unit 22 creates an ID based on the one or more of the read key information items. In the present embodiment, the ID is called a one-time password. The encryption and ID creation unit 22 outputs the generated ciphertext and ID (one-time password) to the transmission unit 23.

The transmission unit 23 is a transmission means configured to transmit the ciphertext and one-time password generated by the encryption and ID creation unit 22 to the reception terminal 30. The transmission unit 23 transmits the ciphertext and one-time password to the reception terminal 30 via a communication network. The configuration of the transmission terminal 20 has been described above.

As shown in FIG. 1, the reception terminal 30 includes a storage unit 31, a reception unit 32, a decryption information acquisition unit 33, and a decryption unit 34.

The storage unit 31 is a storage means configured to store a one-time password and decryption information corresponding to each container contained in the key medium set in association with each other. In the present embodiment, the storage unit 31 stores key information items corresponding to all containers contained in the key medium set in association for each container. That is, the storage unit 31 stores key information items of DNA barcodes contained in the same container in association with each other. Here, the stored key information is not limited to the base sequence, but may be data converted into the bit data described above. As described above, the one-time password corresponds to any of key information items of the container. In addition, the common key is any key information item of the same container or information generated from the key information. Therefore, when key information items corresponding to all containers contained in the key medium set are stored in association for each container, it is possible to identify (generate) a common key that decrypts the ciphertext transmitted from the transmission terminal 20 from the one-time password transmitted from the transmission terminal 20.

The reception unit 32 is a reception means configured to receive the ciphertext and one-time password from the transmission terminal 20 via a communication network. The reception unit 32 outputs the received ciphertext to the decryption unit 34. The reception unit 32 outputs the received one-time password to the decryption information acquisition unit 33.

The decryption information acquisition unit 33 is a decryption information acquisition means configured to acquire decryption information stored in the storage unit 31, which corresponds to the one-time password received by the reception unit 32. The decryption information acquisition unit 33 inputs a one-time password from the reception unit 32. The decryption information acquisition unit 33 reads key information stored in the storage unit 31 in association with key information which is an input one-time password and acquires it as decryption information. That is, the container used for encryption is identified by the one-time password, and key information of the DNA barcode contained in the container is acquired. The decryption information acquisition unit 33 outputs the acquired key information to the decryption unit 34. Here, when encrypted key information as a one-time password is used, it is decrypted to the original base sequence or bit data, and decryption information stored in the storage unit 31 is acquired.

The decryption unit 34 is a decryption means configured to decrypt the ciphertext received by the reception unit 32 using decryption information acquired by the decryption information acquisition unit 33. The decryption unit 34 inputs ciphertext from the reception unit 32. The decryption unit 34 inputs decryption information from the decryption information acquisition unit 33.

The decryption unit 34 decrypts ciphertext according to a preset and stored encryption algorithm and obtains plaintext using one or more key information items input as decryption information from the decryption information acquisition unit 33 as a common key. The preset and stored encryption algorithm is, for example, determined in advance by the information recipient as described above.

The decryption unit 34 may generate a common key from one or more key information items input as decryption information from the decryption information acquisition unit 33 and decrypt ciphertext. Here, in this case, a common key generation rule may be determined in advance (for example, setting the length of a DNA barcode as key information, the type of the base at the beginning, key information of a one-time password at the beginning, etc.), and a common key may be generated according to the generation rule. Alternatively, a plurality of common keys may be generated for each order of key information items and decryption may be attempted for all of them. The plaintext decrypted by the decryption unit 34 is appropriately used by the reception terminal 30 or the like. The configurations of the analysis device 10, the transmission terminal 20 and the reception terminal 30 according to the present embodiment have been described above.

Next, using a schematic diagram showing exchanges between the information recipient and the information transmitter in FIG. 2 and flowcharts in FIG. 3 and FIG. 4, exchanges between the information recipient and the information transmitter according to an embodiment of the present embodiment will be described. A case in which a key information pair K is present in a container C will be described, but in the present embodiment, the key information K is not limited to the pair.

The exchange includes an encryption method and a decryption method according to the present embodiment. The encryption method includes an operation method of the encryption system 1 and is a method of encrypting plaintext, and is shown in the flowchart in FIG. 3. The decryption method is an operation method of the reception terminal 30 and is a method that decrypts the ciphertext encrypted by the encryption method, and is shown in the flowchart in FIG. 4.

Figure 2:
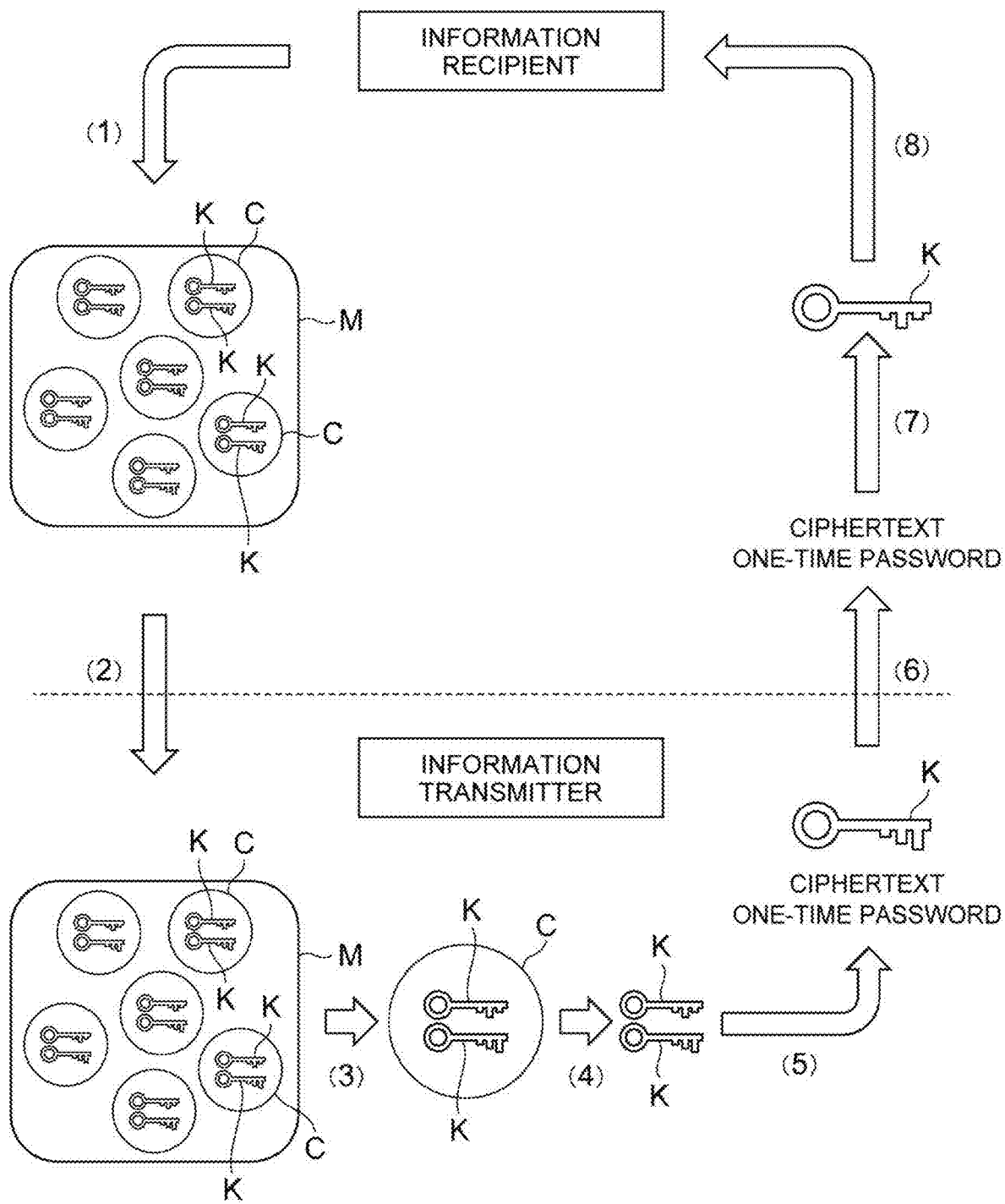
FIG. 2 is a schematic diagram showing exchanges between an information recipient and an information transmitter.

First, the information recipient generates a plurality of containers C and generates a key medium set M containing the plurality of containers C ((1) in FIG. 2). Examples of the key medium set M include the following. A compound is used as a key medium. When a nucleic acid as a polymer which is a biopolymer is used as a compound, key information can be recorded as sequence information of base sequences. For example, 00 is replaced with A, 01 is replaced with G, 10 is replaced with C, and 11 is replaced with T, a nucleic acid having a specific base sequence is synthesized, and the information transmitter that has received the synthesized nucleic acid analyzes a sequence of the nucleic acid, replaces A with 00, G with 01, C with 10, and T with 11 (bit data) which are present in the sequence, and thus can acquire key information. In the above case, key information recorded in the container is prepared in advance and a nucleic acid having a base sequence corresponding to key information is synthesized.

In this case, in the reception terminal 30 in FIG. 1, key information items corresponding to all containers C contained in the key medium set M are stored in association for each container in the storage unit 31. That is, key information items K of DNA barcodes contained in the same container C are stored in association with each other. The storage is performed by the information recipient inputting information to the reception terminal 30.

Although the synthesized nucleic acid fragment can be used without change, it may be inserted into vectors that are replicated in cells such as plasmid vectors, virus vectors, cosmid vectors, and fosmid vectors and then used as a key.

A method of recording information using DNA is not particularly limited, and is described in, for example, Biotechnology Progress 23, 501-505 (2007) published by the inventors, and methods commercially available from Twist Bioscience and the like may be used. Regarding a method in which a nucleic acid (DNA) in which information is recorded is prepared as a key, for example, the following method can be used.

A short DNA molecule (DNA barcode) having a common sequence for PCR amplification and DNA sequencing analysis at both ends of a specific artificial base sequence (information) and in which information is recorded is prepared.

Such a DNA barcode is used in an approach for labeling cells and molecules, and the inventors have developed a Barcode Fusion Genetics (BFG) method in which events related to a plurality of molecules can be comprehensively measured, and published the method (Molecular Systems Biology 12, 863(2016)).

In the BFG method, DNA barcodes in a specific molecular pair state can be simultaneously measured. For example, according to application to a yeast two-hybrid method, 2.5 million human protein molecule pairs or more have been already successfully measured, and linked pairs of DNA barcodes are acquired.

In the embodiment of the present invention, pair information regarding the linked pair of DNA barcodes (information on which DNA barcode is linked to which DNA barcode, that is, association for each container) is treated as private information of the information recipient.

A common sequence for PCR amplification (Primer F and Primer R) may be applied to these DNA barcodes at both ends of the base sequence recorded as information so that these DNA barcodes can be amplified through PCR.

During delivery to the information transmitter, the linked pair of DNA barcodes are divided into two DNA barcodes before linking, and a container containing the divided DNA barcodes is generated, and is delivered as a key medium set M. The reason for delivery in a divided manner will be described below.

When the linked pair of DNA barcodes remains without change, in the linked pair of DNA barcodes spatially constrained in a limited space, even if the spatial constraint of the container is released, for example, when the container is composed of cells, even if cells are crushed, pair information is maintained and the pair information cannot be used as private information. On the other hand, when the linked pair of DNA barcodes is divided, pair information is maintained if it is present as a container, and if the spatial constraint of the container is released, barcodes are no longer physically bound as a pair, and when the spatial constraint in a plurality or all of containers is released once in the key medium set, and information as a pair for each container disappears. That is, it is unknown which DNA barcodes are present in one container as a pair. In order to analyze DNA barcode information, it is necessary to release the spatial constraint for each container. Therefore, if analysis of DNA barcode information on a plurality or all of containers that constitute the key medium set is attempted all at once, information as a pair in each container disappears. The information itself on the type of a DNA barcode (key) present in the container is also important private information.

Since the information recipient is familiar with information on all DNA barcodes present in the container, in this case, information on a pair of DNA barcodes, even if the spatial constraint is released, if there is one DNA barcode information item, all DNA barcodes present in the container, in this case, a pair of DNA barcodes, can be identified.

As will be described below, the information transmitter may arbitrarily select one container from among a great number of containers, and use information obtained by analyzing the pair of DNA barcodes constrained in the container as a key. Since analysis is performed on one container, the pair of DNA barcodes can be identified even if the constraint by the container is released.

On the other hand, even if a (malicious) third party analyzes one by one, it can identify a pair of DNA barcodes constrained in the container, but it is not realistic to analyze all of a great number of containers in reality. When a plurality or all of a great number of containers are collectively analyzed, as described above, since pair information disappears, it is not possible to identify DNA barcodes constrained in the container, in this case, a pair of DNA barcodes. As a result, it is almost impossible for a third party to identify one container selected by the information transmitter and identify DNA barcodes present in the container. Even if one DNA barcode is known from a one-time password using one DNA barcode delivered from the information transmitter to be described below, it is very difficult to identify a container and identify a pair of DNA barcodes.

An example of a method of dividing a linked pair of DNA barcodes will be described below with reference to FIG. 5.

In a DNA molecule having a circular structure (the left in FIG. 5), L has DNA barcode 1 (key 1) information, and R has DNA barcode 2 (key 2) information, which are present as a pair. In the DNA molecule, specific sequences causing recombination with a DNA recombinase Cre, loxP and lox2272, are arranged. According to treatment with the enzyme Cre, the molecule is divided into DNAs having a circular structure of L (key 1) and R (key 2) at the position of the specific sequences, as shown on the right in FIG. 5.

These two or more types of keys need to be spatially constrained so that they are not separated in the container. However, for example, since living cells (that the information recipient has) into which a DNA molecule having a circular structure as shown on the left in FIG. 5 is introduced are treated with the enzyme Cre, keys are present in living cells as DNA having a circular structure of L (key 1) and R (key 2) constrained in living cells (for delivery to the information transmitter). As shown on the left in FIG. 5, when two DNA molecules having a circular structure is introduced into living cells, living cells having four types of keys can be obtained.

Of course, a desired number of DNA molecules that have been divided or that have a circular structure containing one DNA barcode may be introduced into living cells one by one. When a marker for drug resistance or the like is inserted into a DNA molecule having a circular structure, it can be confirmed whether the DNA molecule is introduced into living cells.

Examples of living cells include prokaryotic cells such as bacterial cells, and eukaryotic cells such as yeasts, filamentous fungus, insect cells, mammal cells and plant cells.

Specific examples of prokaryotes include prokaryotes belonging to the genus *Escherichia, Brevibacillus, Serratia, Bacillus, Microbacterium, Brevibacterium, Corynebacterium* or *Pseudomonas*.

Examples of yeasts include yeasts belonging to a genus selected from the group consisting of *Saccharomyces, Schizosaccharomyces, Kleberomyces, Trichosporon, Siwaniomyces, Pichia, Candida, Yarrowia* and *Hansenula*.

Examples of filamentous fungi include filamentous fungi belonging to a genus selected from the group consisting of *Aspergillus, Penicillium* and *Mucoa*.

Examples of insect cells include insect cells of Lepidoptera such as *Drosophila* S2 and *Spodoptera* Sf9.

Examples of animal cells include CHO, COS and human cell lines.

Examples of plant cells include cells of cereals, potatoes, wheat, rice, corn, tobacco, and barley.

Introduction of nucleic acids as keys into such living cells can be performed by known methods, that is, transformation, transfection, transduction, virus infection, a gene gun method, lipofection, electroporation, microinjection, or the like.

These living cells into which nucleic acids as keys are introduced are cultured according to respective known methods, and a culture solution is stored as a stock, and as necessary, these may be mixed and delivered to the information transmitter.

Figure 6:
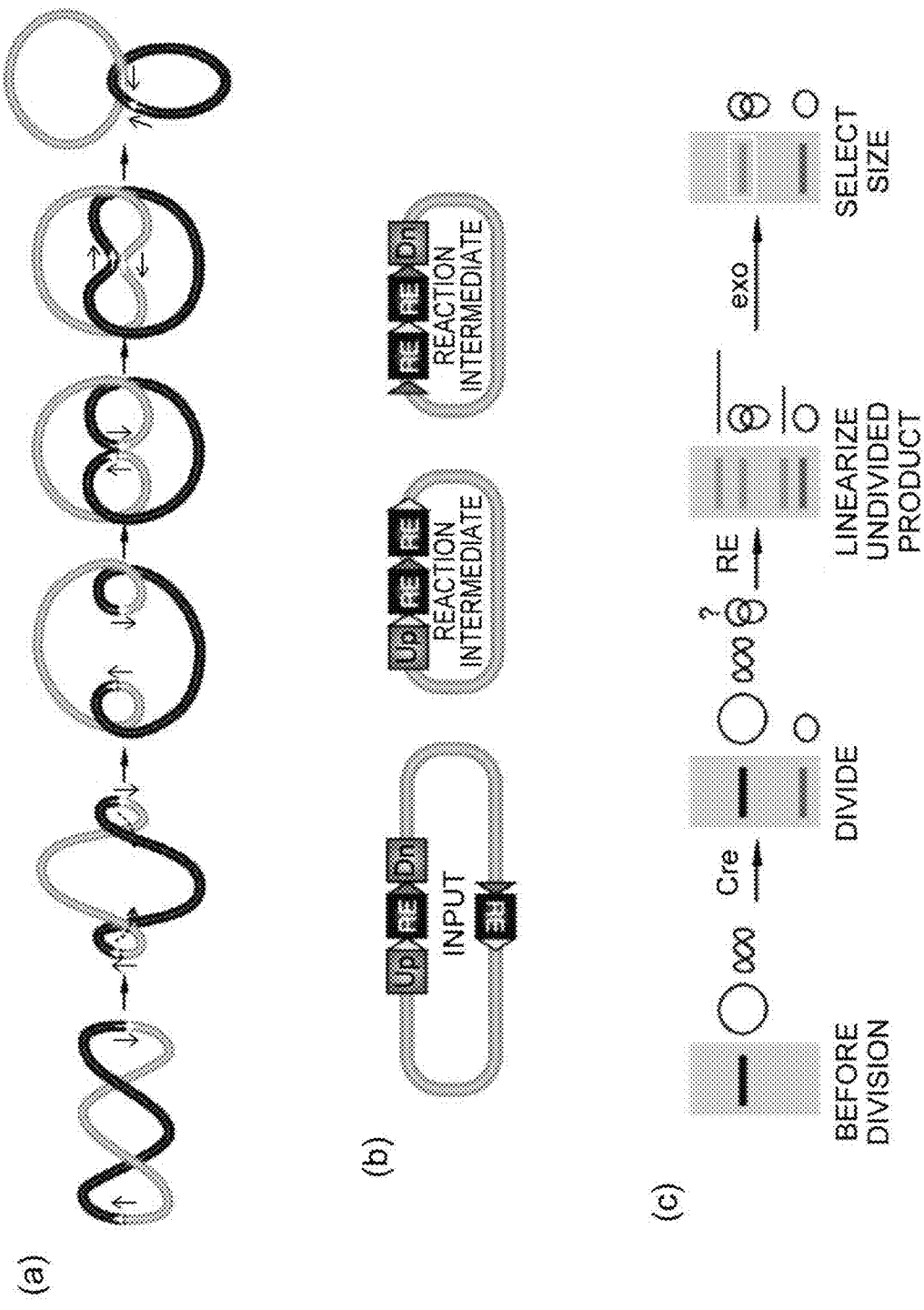
FIG. 6 is a schematic diagram showing an example of a method of dividing a linked pair of DNA barcodes according to another embodiment of the present invention.

The above example is a method of spatial containment by physical containment using living cells. However, when circular DNA chain molecules shown in FIG. 6 are used, keys can be spatially constrained so that they are not separated without using living cells.

Figure 5:
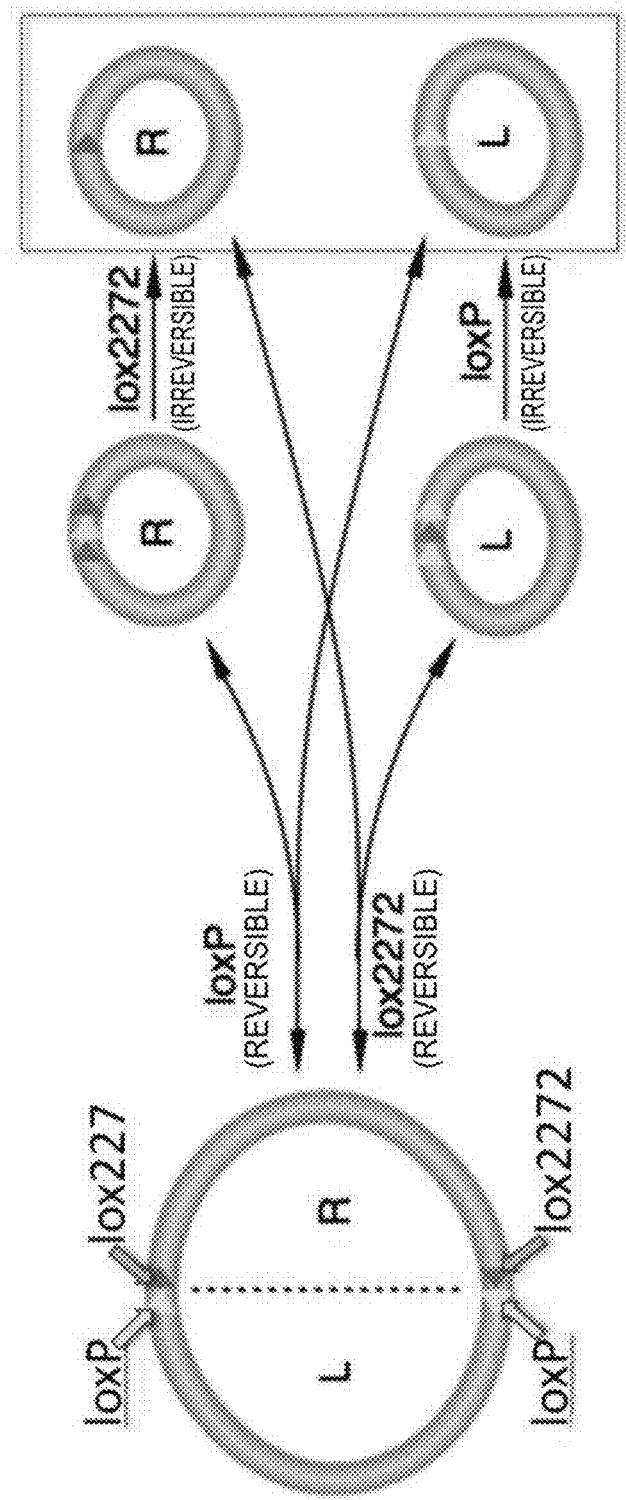
FIG. 5 is a schematic diagram showing an example of a method of dividing a linked pair of DNA barcodes according to an embodiment of the present invention.

In the DNA molecule having a circular structure shown on the left in FIG. 5, when a DNA molecule having a circular structure has a twisted structure such as a supercoil structure as shown on the left in FIG. 6(a), the circular DNA has a circular DNA chain structure as shown on the right in FIG. 6(a) when it is cut due to recombination. When a restriction enzyme site is introduced between lox sequences (the left in FIG. 6(b)), after the enzyme Cre treatment, all reaction intermediates (at the center and right in FIG. 6(b)) with a remaining restriction enzyme site can be cut with the restriction enzyme, and linearized. Therefore, when a DNA exonuclease treatment is additionally performed, only linearized DNAs can be selectively disassembled. Molecules remaining in these treatment solutions are only circular DNAs (L (key 1) and R (key 2) on the right in FIG. 5 and the circular DNA chain structure on the right in FIG. 6(a)) in which a segmentation reaction has completely occurred, and a molecule group in which two circular DNAs are linked by a chain structure can be separated and isolated through electrophoresis based on the size of the molecular weight (the right in FIG. 6(c)).

A molecule in which two circular DNAs are linked by a chain structure can remain in a constrained state without physical containment using living cells described above.

Next, the generated key medium set M is delivered from the information recipient to the information transmitter ((2) in FIG. 2). The delivery is performed physically. In the case of the container using living cells, a culture solution in which these living cells are cultured may be delivered. When a circular DNA chain is used, a form that is suspended in a solution in which a circular DNA chain can be stably maintained or a form in which the suspension is impregnated into paper or the like may be delivered.

Next, the information transmitter selects one container C from the key medium set M ((3) in FIG. 2). Regarding a selection method, when the container is a culture solution, based on information of the information recipient, a culture solution of the living cells is applied to an agar medium suitable for growth of living cells, and the cells are cultured, and one of the colonies that appears may be selected.

In the case of the circular DNA chain, the DNA is introduced into microorganisms such as *E. coli*, and similarly, culture is performed under conditions suitable for microorganisms such as *E. coli*, and one of the colonies that appears may be selected.

Examples of a method of introducing the microorganism include methods using calcium ions [Proc. Natl. Acad. Sci. USA, 69, 2110 (1972)], protoplast methods (Japanese Unexamined Patent Publication No. S63-248394), and methods described in Gene, 17, 107 (1982), Molecular & General Genetics, 168, 111 (1979).

Figure 3:
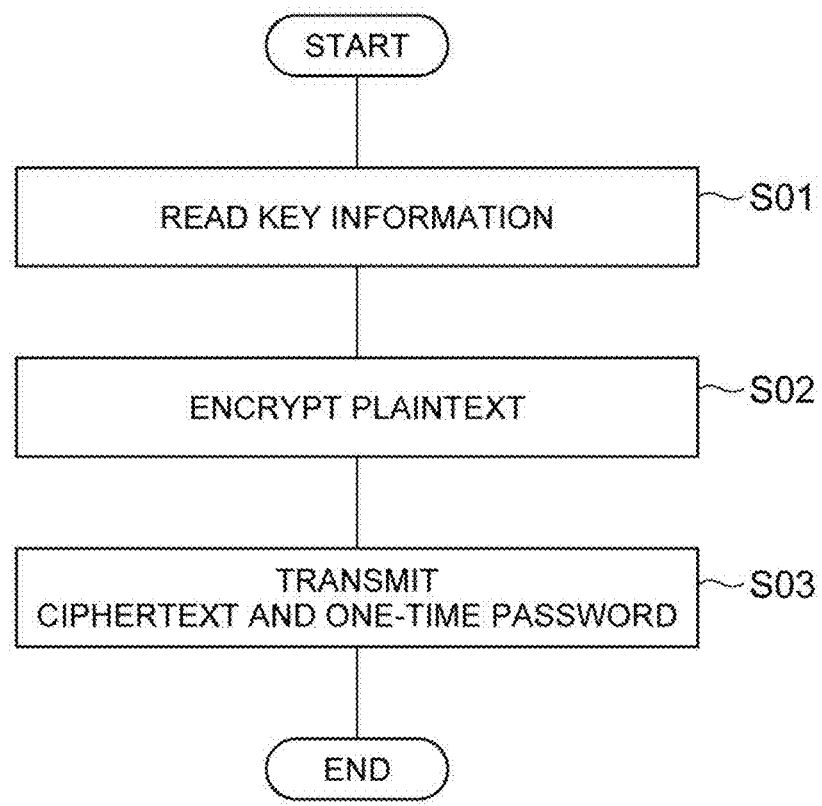
FIG. 3 is a flowchart showing an encryption method according to an embodiment of the present invention.

Next, the analysis device 10 reads a base sequence as key information K from two DNA barcodes included in the selected container C ((4) in FIG. 2, S01 in FIG. 3, key information reading step).

The spatial constraint of one selected container C is released, and key information is obtained from the DNA barcode that has been constrained as a container. Regarding a polymer in which information is recorded, when a nucleic acid (DNA) is used as a key, key information can be obtained by the following method.

PCR is performed using a common sequence for PCR amplification (Primer F and Primer R) preset by the information recipient at both ends of the base sequence recorded as information, and a nucleic acid (DNA) as a key is amplified. The common sequence information for PCR amplification is obtained from the information recipient when the container is obtained. The base sequence of the amplified nucleic acid (DNA) as a key is analyzed by a general method such as DNA sequencing analysis.

As a specific example, the following method can be used.

A colony formed from a single container is arbitrarily selected, and picked up with a toothpick, and aseptically added to 1.5 ml tubes containing 9.2 μL of sterile water, 0.4 μL of Primer F, 0.4 μL of Primer R, and 10 μL of PrimeSTAR (registered trademark) Max DNA Polymerase (commercially available from Takara Bio Inc.). The tubes are set in a thermal cycler (Veriti commercially available from Applied Biosystems), and for example, PCR is performed by repeating a PCR profile at 94 to 98° C. for 5 to 10 seconds, at 50 to 65° C. for 5 to 15 seconds, and at 70 to 75° C. for 5 to 30 seconds over 5 to 30 cycles. Before repetition of the cycle of the PCR profile starts, a treatment may be performed at 94 to 98° C. for 30 to 60 seconds. In addition, after repetition of the cycle of the PCR profile, a treatment may be performed at 70 to 75° C. for 60 to 120 seconds.

11 μL of sterile water, 4 μL of 5× Sequence Buffer, 1 μL of Primer R (10 pmol) and 1 μL of BigDye (registered trademark) Terminator v3.1 Ready Reaction Mix (commercially available from Thermo Fisher Scientific Inc.) were added to 3 μL of amplified DNA fragments (200 to 600 ng/μL), and for example, PCR is performed by repeating a PCR profile at 94 to 98° C. for 5 to 10 seconds, at 50 to 65° C. for 5 to 15 seconds, and at 55 to 65° C. for 60 to 250 seconds over 10 to 30 cycles. Before repetition of the cycle of the PCR profile starts, a treatment may be performed at 94 to 98° C. for 30 to 60 seconds. 5 μL of 125 mM EDTA, and 60 μL of 100% ethanol were added to 20 μL of the sequence reaction end solution prepared through this PCR, mixed, and allowed to stand in a dark place for 15 minutes. After standing, the mixture is centrifuged at 10,000×g for 20 minutes, and the supernatant is removed with a pipette. 60 μL of 70% ethanol is added to the precipitate fraction, the mixture is centrifuged at 10,000×g for 10 minutes, and the supernatant is removed with a pipette. The result is allowed to stand in an incubator at 65° C. for 10 minutes and dried. After drying, 20 μL of Hi-Di formamide is added thereto and the mixture is sufficiently stirred. A total amount of the stirring solution is added to a 96-well plate for sequencing, and is set in the sequencer (3730 DNA Analyzer commercially available from Applied Biosystems), and the base sequence is confirmed.

The read key information K is input from the analysis device 10 to the key information input unit 21 of the transmission terminal 20. As described above, the base sequence may be converted into bit data by the key information input unit 21. Specifically, the base sequence of a region recorded as information is converted into bit data, for example, by replacing A with 00, replacing G with 01, replacing C with 10, and replacing T with 11, and thus key information for encryption may be acquired as bit data.

Next, in the transmission terminal 20, the encryption and ID creation unit 22 encrypts plaintext using one of the key information K and generates ciphertext ((5) in FIG. 2, S02 in FIG. 3, encryption step). Next, the transmission unit 23 transmits a one-time password based on the ciphertext and the other of the key information K to the reception terminal 30 via a communication network ((6) in FIG. 2, S03 in FIG. 3, transmission step).

Figure 4:
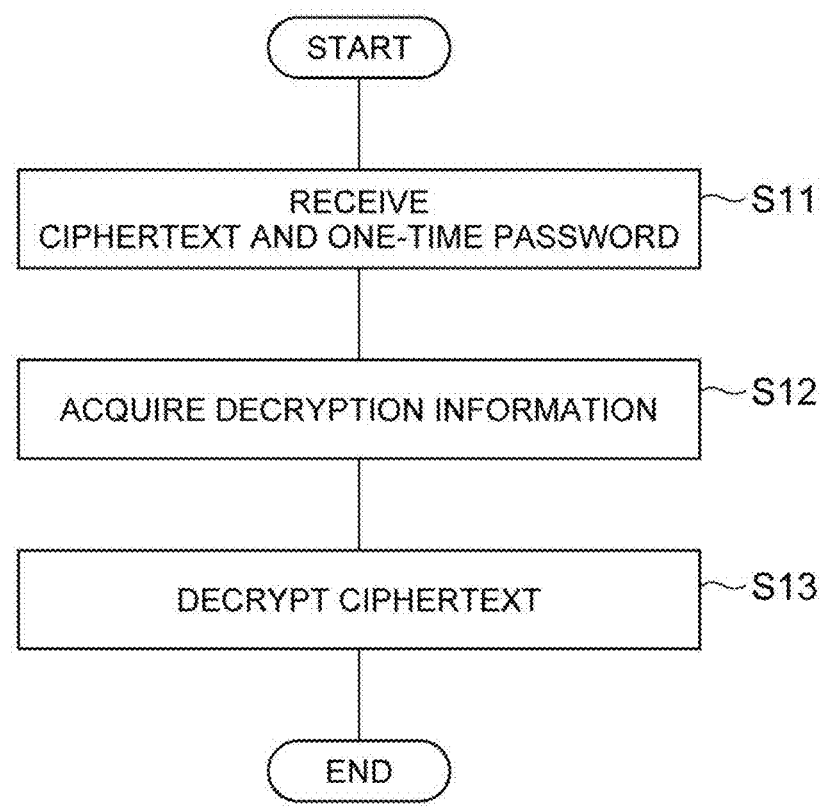
FIG. 4 is a flowchart showing a decryption method according to an embodiment of the present invention.

In the reception terminal 30 to which the ciphertext and one-time password are transmitted, the reception unit 32 receives the ciphertext and one-time password ((6) in FIG. 2, S11 in FIG. 4, reception step). Next, the decryption information acquisition unit 33 acquires the key information K which is decryption information stored in the storage unit 31, which corresponds to the received one-time password ((7) in FIG. 2, S12 in FIG. 4, decryption information acquisition step). Next, the decryption unit 34 decrypts the received ciphertext using the acquired decryption information ((8) in FIG. 2, S13 in FIG. 4, decryption step). The exchange between the information recipient and the information transmitter in the present embodiment has been described above.

As described above, in the present embodiment, key information of each DNA barcode of one container C is read from a plurality (for example, tens of thousands) of containers C contained in the key medium set M and used for encryption. Therefore, since it is difficult for a third party to identify key information used for encryption, more secure encryption can be performed. In addition, during decryption, decryption is performed using decryption information stored in correspondence to the received one-time password. Therefore, it is possible to reliably decrypt the encrypted information encrypted by the above encryption method.

In addition, a DNA barcode in which key information is recorded as in the present embodiment may be used. With such a configuration, it is possible to read key information easily and reliably, and as a result, one embodiment of the present invention can be implemented easily and reliably.

However, the compound which is contained in the container and in which key information is recorded does not necessarily need to be a nucleic acid, and for example, a biopolymer other than a nucleic acid such as a peptide may be used. When the peptide is used as a compound, the sequence of amino acid residues can be used as key information. Short peptides can be synthesized by a simple organic synthetic chemistry technique. Even if a peptide is used, as described above, the amino acid residues may be replaced with bit data. Even though a biopolymer is used, it is possible to reliably make it difficult to identify key information, and it is possible to reliably perform more secure encryption.

In addition, a synthetic polymer may be used as a compound which is contained in the container and in which key information is recorded. For example, optical information recording mediums such as a compact disc (CD), a digital versatile disc (DVD), and a Blu-ray (registered trademark) Disc can be used. Regarding a recording and reproducing method using an optical information recording medium, methods already known as CD, DVD, or Blu-ray Disc may be used. In order to record and reproduce information, a laser beam may be used. In the method using an optical information recording medium, since information is stored as bit data, there is no need to convert info Illation, and the reproduced information can be used as key information without change.

Examples of optical information recording mediums include those in which an organic dye recording film is formed on a polycarbonate substrate using a sputtering device (HSM-552 commercially available from Shimadzu Corporation) according to a DC magnetron sputtering method.

In addition, a low molecular compound may be used as a compound which is contained in the container and in which key information is stored. In this case, the type of the low molecular compound, the number of hydroxyl groups present in the compound, and the like can be used as key information. As described above, regarding the compound which is contained in the container and in which key information is stored, a compound that is selected from the group consisting of low molecules, synthetic polymers and biopolymers can be used as long as it can record information.

Regarding a method of spatially constraining, that is, a method of generating a container, a method of encapsulating a compound in which information is recorded in a container such as a microcapsule may be used. This method can be used not only for a compound in which information is recorded such as an optical information recording medium, but also for any compound in which information is recorded such as the nucleic acid.

Regarding methods of producing a microcapsule containing a core material (compound (key) in which information is recorded) and encapsulating keys, known methods may be used.

Examples of known methods include chemical methods such as an interfacial polymerization method, a suspension polymerization method, a dispersion polymerization method, an in-situ polymerization method, an emulsion polymerization method and an in-liquid curing method, physicochemical methods such as an in-liquid drying method, a phase inversion emulsification method, a heterocoagulation method and a coacervation method, and additionally, a high-speed air-flow impact method, and a spray drying method.

The interfacial polymerization method is a method of dissolving monomers that form a capsule film in an incompatible two-phase solvent and synthesizing a film by a polymerization reaction at the interface between two liquids.

The suspension polymerization method is a polymerization method that is performed by mechanically stirring a monomer phase that is insoluble in water with an aqueous phase, and suspending it, and has high monodispersity.

The dispersion polymerization method is a typical method of synthesizing monodispersed polymer fine particles with a micro size. The polymerization starts in a homogeneous solution in which all monomers, initiators, and dispersion stabilizers are dissolved in a medium, and polymers generated when the polymerization starts are precipitated, and aggregate to form particles.

The in-situ polymerization method is a method in which monomers and a reaction initiator are dissolved in any one of two incompatible phases, the monomers are subjected to a polymerization reaction at the interface of the core material, and a uniform film is formed on the surface of the core material.

The emulsion polymerization method is a polymerization method in which a medium such as water, monomers that are hardly soluble in a medium, and a surfactant are mixed and emulsified, and can be dissolved (a polymerization initiator is added).

The in-liquid curing method is a method in which a substance that is desired to form microcapsules is dispersed in a polymer solution in advance, the solution is adjusted to have a desired shape, and the polymer is cured to form a coating.

The in-liquid drying method is a method in which a solution or solid as a core material is dispersed in a solvent in which a polymer as a shell agent is dissolved, and dispersed in a solvent that is immiscible with the solvent, and additionally, the first solvent is gradually removed and the polymer is precipitated at the interface of the core material.

The phase inversion emulsification method is a method in which, in a dispersed phase in which a core material is dispersed, a continuous phase that is not mixed with the phase is gradually inverted, and after the phase inversion, a suspension polymerization or in-liquid drying method is performed.

The heterocoagulation method is a method in which a core material and shell-forming particles are suspended in a continuous aqueous phase, conditions in which electrification is performed with different charges are selected, an electrostatic interaction between both particles occurs, and an aggregate in which the shell-forming particles are attached to the surface of the core material is formed.

The coacervation method is a method that uses a phenomenon in which a polymer solution is separated into a more highly dispersed phase and a dilute continuous phase due to environmental change, and examples thereof include a method using gelatin.

The high-speed air-flow impact method is a method in which core material particles and smaller fine particles are caused to flow in a fluid at a high speed, hydrodynamic energy is used, and the fine particles are applied to the surface of the core material particle to form a composite and fixed.

The generation and delivery of the key medium set M when a container encapsulated in microcapsules is used may be performed by delivering a solution in which microcapsules are suspended as in the above embodiment. In addition, in this case, the information transmitter may select one container using a microscope or the like.

Regarding reading of key information when using an optical information recording medium as a compound, the optical information recording medium is removed from the selected microcapsule, irregularities on the surface are observed according to scanning probe microscope observation (SPM) directly, and thus key information can be directly acquired as bit data. In addition, key information can be acquired as bit data by using a reading device using a laser beam, such as a CD, a DVD, and a Blu-ray Disc.

As described above, the container may be composed of cells or capsules containing a compound or circular DNA chains. Accordingly, the set has a plurality of keys composed of compounds which are physically associated with each other in which different information items are recorded. A method of physically associating with each other may be a method of containment in a limited space such as a cell and a capsule, or a method in which a linked key such as a circular DNA chain is cut off during decryption, and a mutual link is released. In such a configuration, it is possible to easily and reliably generate a container which is a set including a plurality of key information items including compounds which are included in the key medium set and physically associated with each other in which different key information items are recorded, and as a result, one embodiment of the present invention can be implemented easily and reliably.

Here, in the above embodiment, encryption is performed according to common key encryption. However, encryption may be performed according to public key encryption. For example, encryption may be performed by an encryption algorithm such as RSA. Even in such a case, ciphertext generated by a public encryption algorithm and a one-time password may be transmitted to the information recipient.

EXAMPLES

The present invention will be described below in more detail with reference to examples. However, the present invention is not limited to the following examples.

Example 1: Production of Nucleic Acid Key

According to the following method, a stable circular DNA molecule was constructed, separated into two circular DNA molecules in yeast cells with high efficiency, and a container having two types of keys (DNA barcodes) spatially constrained was produced.

According to the method described in Molecular Systems Biology 12, 863 (2016), the inventors acquired more than 2.5 million linked DNA barcodes (referred to as Uptag and Dntag) of human protein molecule pairs.

Using the linked Uptag and Dntag, in the following method, a DNA vector in which loxP and lox2272 for separation into two circular DNA molecules were specifically arranged was constructed.

Figure 7:
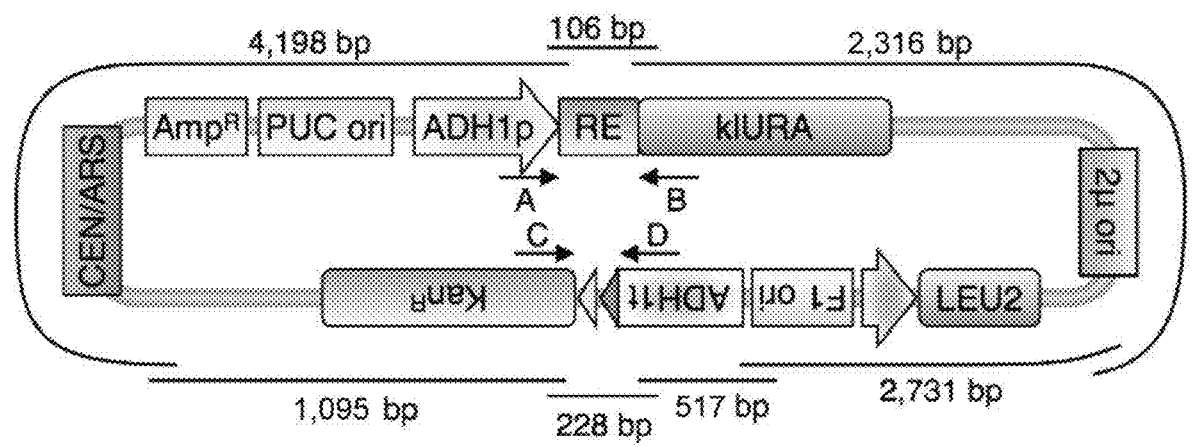
FIG. 7 is a schematic diagram showing a backbone DNA vector pNZM1300 for constructing a stable circular DNA molecule according to Example 1.
Figure 8:
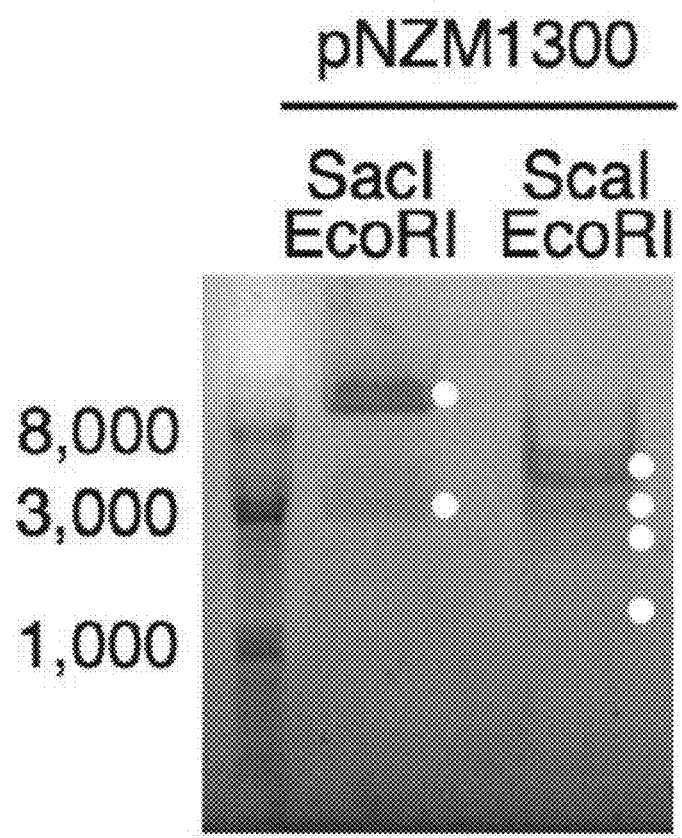
FIG. 8 shows an image of a backbone DNA vector pNZM1300 cut with a restriction enzyme and electrophoresed in Example 1.

FIG. 7 shows a backbone DNA vector pNZM1300 for constructing stable circular DNA molecules. pNZM1300 was constructed by chemically synthesizing DNA fragments of 2731 bp (Fragment 1: 1 to 2731 of SEQ ID NO. 1), 517 bp (Fragment 2: 2682 to 3198 of SEQ ID NO. 1), 228 bp (Fragment 3: 3149 to 3376 of SEQ ID NO. 1), 1095 bp (Fragment 4: 3327 to 4421 of SEQ ID NO. 1), 4198 bp (Fragment 5: 4372 to 8569 of SEQ ID NO. 1), 106 bp (Fragment 6: 8520 to 8625 of SEQ ID NO. 1), 2316 bp (Fragment 7: 1 to 50 and 8576 to 10841 of SEQ ID NO. 1) and assembling them. Correct construction was confirmed according to a restriction enzyme treatment (FIG. 8) and Sanger sequencing. The complete sequence of pNZM1300 is shown in SEQ ID NO. 1.

Figure 9:
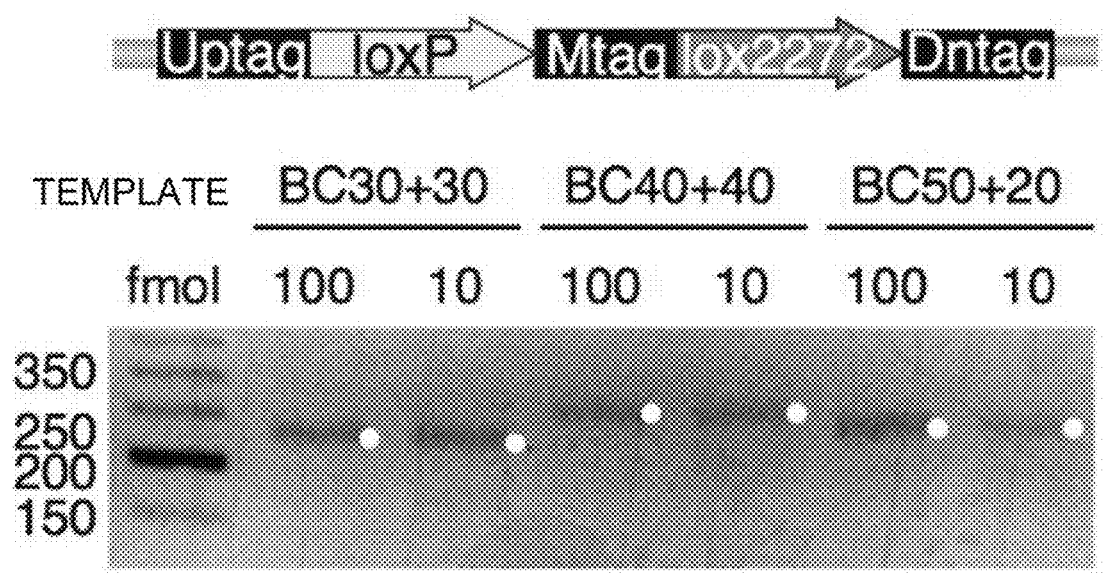
FIG. 9 shows an image of a pair of DNA barcodes (Uptag and Dntag) amplified and electrophoresed in Example 1.

FIG. 9 shows an example of the results obtained by amplifying the acquired pair of DNA barcodes (Uptag and Dntag). The linked pair of DNA barcodes was modified so that loxP-random sequence (Mtag)-lox227 was interposed between Uptag and Dntag. Mtag was inserted for parity check when combination information of Uptag and Dntag was identified. No Mtag remained in the circular DNA after the segmentation treatment.

BC30+30 indicates 30 bp for both Uptag and Dntag, BC40+40 indicates 40 bp for both Uptag and Dntag, and BC50+20 indicates 50 bp for Uptag and 20 bp for Dntag.

As shown in FIG. 9, it was confirmed that PCR amplification was able to be correctly performed on a molecular pool having a random sequence in barcode regions for combinations of Uptag and Dntag with various sequence lengths.

Similarly, it was confirmed that PCR amplification was able to be performed on a newly synthesized and linked pair of DNA barcodes.

Figure 10:
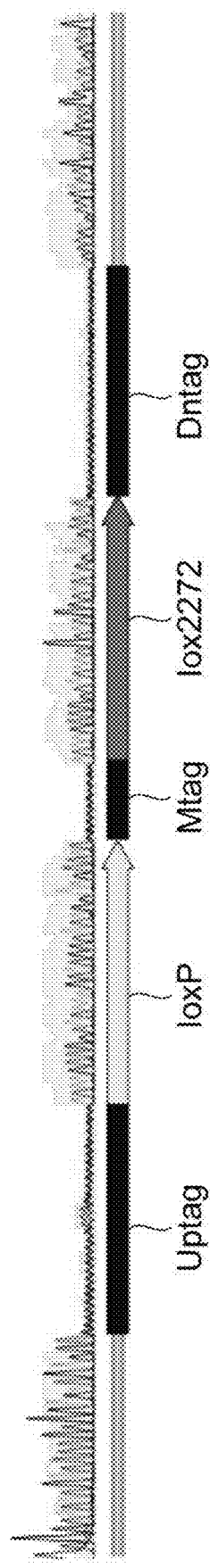
FIG. 10 is a diagram showing the results obtained by confirming the linked pair of DNA barcodes (BC30+30: SEQ ID NO. 2) synthesized in Example 1 according to Sanger sequencing.

FIG. 10 shows the results of a newly synthesized and linked pair of DNA barcodes (BC30+30: SEQ ID NO. 2) as an example of the Sanger sequencing result.

Figure 11:
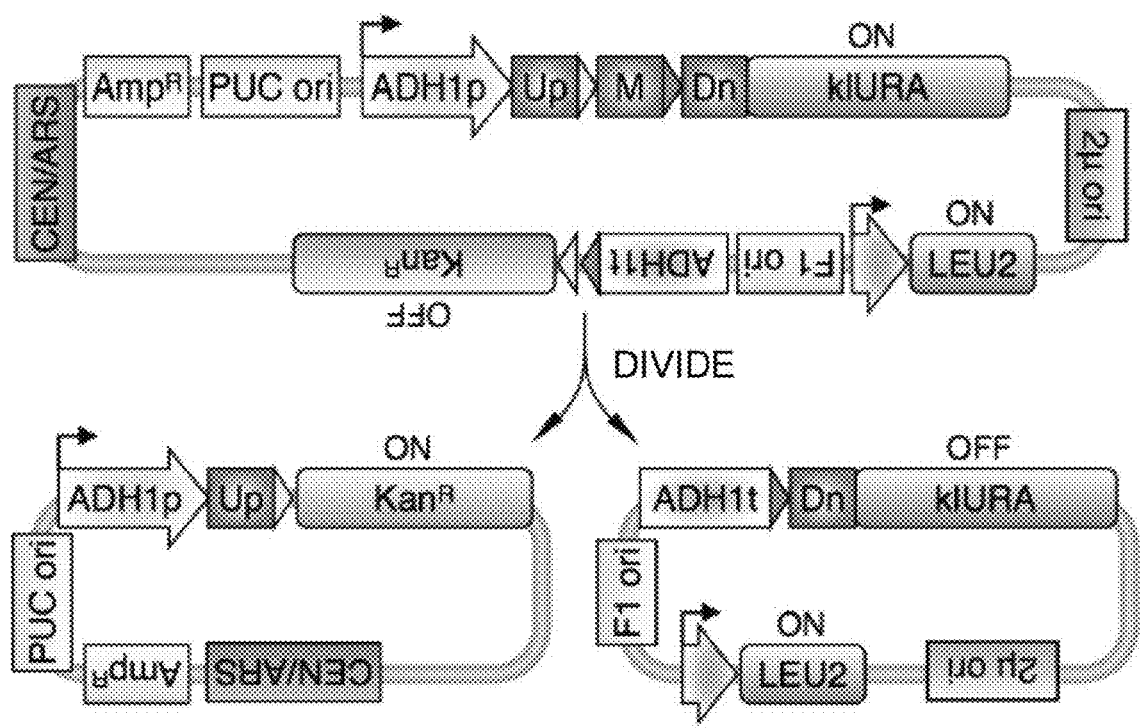
FIG. 11 shows schematic diagrams of a circular DNA vector constructed by inserting a linked DNA barcode containing Uptag and Dntag into an RE region of pNZM1300 and in which the circular DNA vector is divided into irreversible circular DNAs containing Uptag or Dntag due to an enzyme Cre that is induced and expressed.

The linked DNA barcode containing Uptag and Dntag shown in FIG. 9 was inserted into the RE region of pNZM1300 shown in FIG. 10, and a circular DNA vector shown in FIG. 11(a) was constructed.

The circular DNA vector was introduced into histidine, leucine and uracil auxotrophic yeast cells into which a DNA vector having a histidine synthesis gene marker HIS3 that can express galactose-inducible Cre was introduced.

Figure 12:
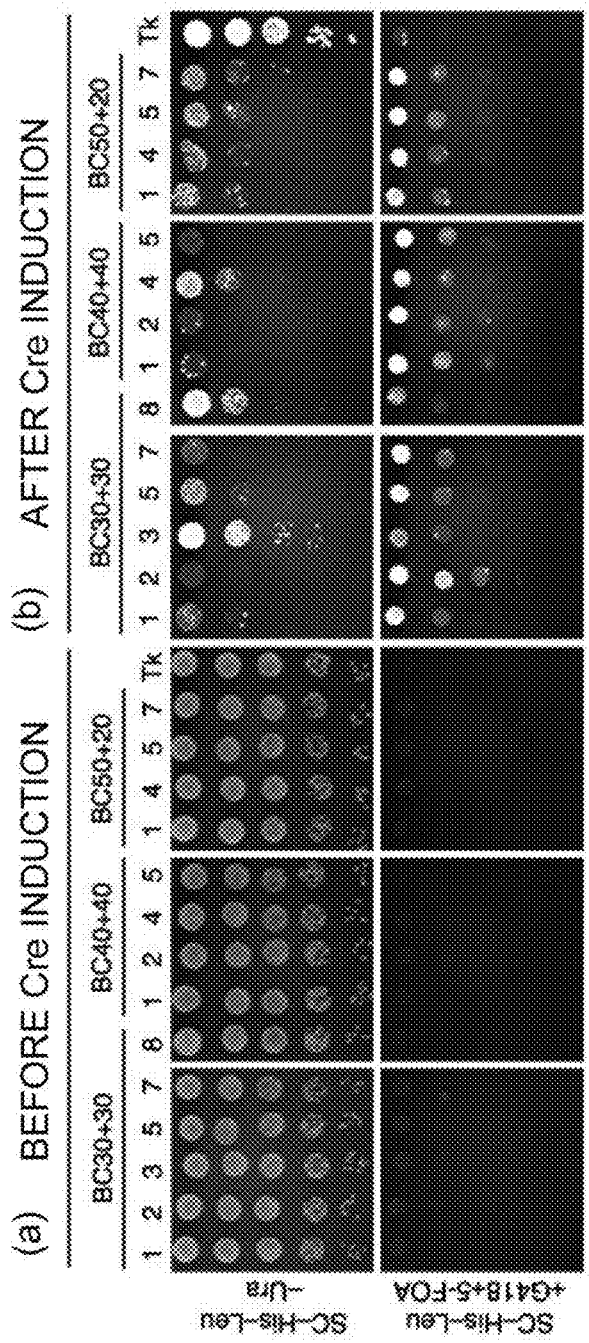
FIG. 12 shows examples of results in which yeast cells having a vector divided into circular DNAs due to an enzyme Cre that is induced and expressed are selected.

The circular DNA vector constantly expressed the leucine synthesis gene LEU2 in yeast cells, and expressed the uracil synthesis gene klURA in which the linked barcode was interposed between gene expression promoters upstream from the linked barcode and exhibiting 5-FOA sensitivity (FIG. 12(a)). On the other hand, no KanR was expressed because transcription termination factors were positioned upstream from the G418-resistant gene KanR with lox2272-loxP therebetween.

Therefore, yeast cells having the circular DNA vector could grow in a leucine- and uracil-deficient medium, and are sensitive to G418 and 5-FOA.

FIG. 12(a) shows an example in which yeast cells having the circular DNA vector were selected in this method.

Yeast cells having the circular DNA vector were cultured in a galactose-containing medium, and a DNA recombinase Cre was induced and expressed.

As described above, division into two via lox2272-loxP was performed with the enzyme Cre as shown in FIG. 5.

When the enzyme Cre was induced and expressed, the circular DNA vector was divided into irreversible circular DNAs containing Uptag or Dntag as shown in FIG. 11(b).

KanR was expressed from an ADH1 promoter in the circular DNA containing Uptag, and LEU2 was constantly expressed from the circular DNA containing Dntag. On the other hand, no klURA was expressed because an ADH1 transcription termination factor was positioned upstream from klURA.

Therefore, when yeast cells which were resistant to G418 and 5-FOA in a leucine-deficient medium but were not able to grow in a leucine- and uracil-deficient medium were selected, it was possible to acquire yeast cells having a vector divided into irreversible circular DNAs containing Uptag or Dntag.

FIG. 12(b) shows an example of the results obtained by selecting yeast cells having a vector divided into circular DNAs using such a selection medium.

According to the above method, 50,000 yeast cells having two types of different DNA barcodes as encryption keys and having completely different encryption keys were produced.

When the method was applied to 2.5 million linked human protein molecule pairs or more that were already acquired, it was possible to produce yeast cells having different encryption keys similarly.

REFERENCE SIGNS LIST

1 Encryption system
10 Analysis device
20 Transmission terminal
21 Key information input unit
22 Encryption and ID creation unit
23 Transmission unit
30 Reception terminal
31 Storage unit
32 Reception unit
33 Decryption information acquisition unit
34 Decryption unit

---

The invention claimed is:

1. An encryption method including an operation method of an encryption system for encrypting encryption target information, the method comprising:
reading a key information item of each compound in one set out of a key medium set including a plurality of sets, wherein the one set includes two or more compounds which are physically associated with each other and are each recorded with a different key information item;
encrypting encryption target information using one or more of the key information items and generates encrypted information; and
transmitting the encrypted information and an ID based on one or more of the key information items to a decryption system.

2. The encryption method according to claim 1, wherein the compound is a compound selected from the group consisting of synthetic polymer and biopolymers.

3. The encryption method according to claim 2, wherein the compound is a nucleic acid, and the key information is a base sequence of the nucleic acid.

4. The encryption method according to claim 1, wherein the set is associated by cells or capsules containing the compound or a circular DNA chain.

5. A decryption method which is an operation method of a decryption system for decrypting encrypted information encrypted by the encryption method according to claim 1, wherein the decryption system includes circuitry configured to store an ID corresponding to each set included in the key medium set and decryption information in association,
wherein the decryption method comprises
a reception step in which the encrypted information and ID are received from the encryption system;
a decryption information acquisition step in which decryption information, which corresponds to the ID received in the reception step is acquired; and a decryption step in which the encrypted information received in the reception step is decrypted using the decryption information acquired in the decryption information acquisition step.

6. The encryption method according to claim 1, wherein the compounds are artificial nucleic acids.

7. The encryption method according to claim 6, wherein the key information item is a base pair sequence of an artificial nucleic acid.

8. The encryption method according to claim 1, further comprising storing the key information item for each compound.

9. An encryption system which encrypts encryption target information, comprising:
a key information reading device configured to read a key information item of each compound of one set out of a key medium set including a plurality of sets, wherein the one set includes two or more compounds which are physically associated with each other and are each recorded with a different key information item; and
circuitry configured to encrypt encryption target information using one or more of-the key information items read by the key information reading device and generate encrypted information; and transmit the encrypted information and an ID based on one or more of the key information items to a decryption system.

10. The encryption system according to claim 9, wherein the compounds are artificial nucleic acids.

11. The encryption system according to claim 9, wherein the key information item is a base pair sequence of an artificial nucleic acid.

12. The encryption system according to claim 9, further comprising a storage that stores the key information for each compound.

13. A decryption system which decrypts the encrypted information encrypted by the encryption system according to claim 9, comprising circuitry configured to:
store an ID corresponding to each set included in the key medium set and decryption information in association;
receive the encrypted information and ID from the encryption system;
acquire decryption information, which corresponds to the ID; and
decrypt the encrypted information using the decryption information.

* * * * *

SEQUENCE LISTING

```
<160> NUMBER OF SEQ ID NOS: 2

<210> SEQ ID NO 1
<211> LENGTH: 10841
<212> TYPE: DNA
<213> ORGANISM: Artificial Sequence
<220> FEATURE:
<223> OTHER INFORMATION: pNZM1300

<400> SEQUENCE: 1
tcgactacgt cgttaaggcc gtttctgaca gagtaaaatt cttgagggaa ctttcaccat      60
tatgggaaat ggttcaagaa ggtattgact taaactccaa caaatggtca ggtcattgag     120
tgttttttat ttgttgtatt tttttttttt tagagaaaat cctccaatat ataaattagg     180
aatcatagtt tcatgatttt ctgttacacc taactttttg tgtggtgccc tcctccttgt     240
caatattaat gttaaagtgc aattcttttt ccttatcacg ttgagccatt agtatcaatt     300
tgcttacctg tattcccttta catcctcctt tttctccttc ttgataaatg tatgtagatt     360
gcgtatatag tttcgtctac cctatgaaca tattccattt tgtaatttcg tgtcgtttct     420
attatgaatt tcatttataa agtttatgta caaatatcat aaaaaaagag aatcttttta     480
agcaaggatt ttcttaactt cttcggcgac agcatcaccg acttcggtgg tactgttgga     540
accacctaaa tcaccagttc tgatacctgc atccaaaacc tttttaactg catcttcaat     600
```

```
ggccttacct tcttcaggca agttcaatga caatttcaac atcattgcag cagacaagat      660
agtggcgata gggttgacct tattctttgg caaatctgga gcagaaccgt ggcatggttc      720
gtacaaacca aatgcggtgt tcttgtctgg caaagaggcc aaggacgcag atggcaacaa      780
acccaaggaa cctgggataa cggaggcttc atcggagatg atatcaccaa acatgttgct      840
ggtgattata ataccattta ggtgggttgg gttcttaact aggatcatgg cggcagaatc      900
aatcaattga tgttgaacct tcaatgtagg gaattcgttc ttgatggttt cctccacagt      960
ttttctccat aatcttgaag aggccaaaac attagcttta tccaaggacc aaataggcaa     1020
tggtggctca tgttgtaggg ccatgaaagc ggccattctt tgattctttt gcacttctgg     1080
aacggtgtat tgttcactat cccaagcgac accatcacca tcgtcttcct ttctcttacc     1140
aaagtaaata cctcccacta attctctgac aacaacgaag tcagtacctt tagcaaattg     1200
tggcttgatt ggagataagt ctaaaagaga gtcggatgca aagttacatg gtcttaagtt     1260
ggcgtacaat tgaagttctt tacgatttt tagtaaacct tgttcaggtc taacactacc      1320
ggtaccccat ttaggaccac ccacagcacc taacaaaacg gcatcagcct tcttggaggc     1380
ttccagcgcc tcatctggaa gtggaacacc tgtagcatcg atagcagcac caccaattaa     1440
atgattttcg aaatcgaact tgacattgga acgaacatca gaaatagctt taagaacctt     1500
aatggcttcg gctgtgattt cttgaccaac gtggtcacct ggcaaaacga cgatcttctt     1560
aggggcagac attagaatgg tatatccttg aaatatatat atatatattg ctgaaatgta     1620
aaaggtaaga aaagttagaa agtaagacga ttgctaacca cctattggaa aaaacaatag     1680
gtccttaaat aatattgtca acttcaagta ttgtgatgca agcatttagt catgaacgct     1740
tctctattct atatgaaaag ccggttccgg cgctctcacc tttccttttt ctcccaattt     1800
ttcagttgaa aaggtatat gcgtcaggcg acctctgaaa ttaacaaaaa atttccagtc      1860
atcgaatttg attctgtgcg atagcgcccc tgtgtgttct cgttatgttg aggaaaaaaa     1920
taatggttgc taagagattc gaactcttgc atcttacgat acctgagtat tcccacagtt     1980
aactgcggtc aagatatttc ttgaatcagg cgccttagac cgctcggcca acaaccaat     2040 tacttgttga gaaatagagt ataattatcc tataaatata acgttttga acacacatga     2100 acaaggaagt acaggacaat tgattttgaa gagaatgtgg attttgatgt aattgttggg     2160
attccatttt taataaggca ataatattag gtatgtagat atactagaag ttctcctcga     2220
ccggtcgata tgcggtgtga ataccgcac agatgcgtaa ggagaaaata ccgcatcagg      2280
aaattgtaag cgttaatatt tgttaaaat tcgcgttaaa ttttttgttaa atcagctcat     2340 tttttaacca ataggccgaa atcggcaaaa tcccttataa atcaaaagaa tagaccgaga     2400
tagggttgag tgttgttcca gtttggaaca agagtccact attaaagaac gtggactcca     2460
acgtcaaagg gcgaaaaacc gtctatcagg gcgatggccc actacgtgaa ccatcaccct     2520
aatcaagttt ttggggtcg aggtgccgta aagcactaaa tcggaaccct aaagggagcc      2580
cccgatttag agcttgacgg ggaaagccgg cgaacgtggc gagaaaggaa gggaagaaag     2640
cgaaaggagc gggcgctagg gcgctggcaa gtgtagcggt cacgctgcgc gtaaccacca     2700
cacccgccgc gcttaatgcg ccgctacagg gagctttgga cttcttcgcc agaggtttgg     2760
tcaagtctcc aatcaaggtt gtcggcttgt ctaccttgcc agaaatttac gaaaagatgg     2820
aaaagggtca atcgttggt agatacgttg ttgacacttc taaataagcg aatttcttat      2880
gatttatgat ttttattatt aaataagtta taaaaaaaat aagtgtatac aaattttaaa    2940
```

```
gtgactctta ggttttaaaa cgaaaattct tattcttgag taactctttc ctgtaggtca    3000
ggttgctttc tcaggtatag catgaggtcg ctcttattga ccacacctct accggcatgc    3060
cgagcaaatg cctgcaaatc gctccccatt tcacccaatt gtagatatgc taactccagc    3120
aatgagttga tgaatctcgg tgtgtatttt atgtcctcag aggacaacac ctgttgtaat    3180
cgttcttcca cacggatcat aacttcgtat aggatacttt atacgaagtt atcagataca    3240
acaccaggac actaggtaat gacgcagata cccaatgaca tataactaga acataacttc    3300
gtatagcata cattatacga agttatatgg gtaaggaaaa gactcacgtt tcgaggccgc    3360
gattaaattc caacatggat gctgatttat atgggtataa atgggctcgc gataatgtcg    3420
ggcaatcagg tgcgacaatc tatcgattgt atgggaagcc cgatgcgcca gagttgtttc    3480
tgaaacatgg caaggtagc gttgccaatg atgttacaga tgagatggtc agactaaact    3540
ggctgacgga atttatgcct cttccgacca tcaagcattt tatccgtact cctgatgatg    3600
catggttact caccactgcg atccccggca aaacagcatt ccaggtatta agaatatc     3660 ctgattcagg tgaaaatatt gttgatgcgc tggcagtgtt cctgcgccgg ttgcattcga    3720
ttcctgtttg taattgtcct tttaacagcg atcgcgtatt tcgtctcgct caggcgcaat    3780
cacgaatgaa taacggtttg gttgatgcga gtgattttga tgacgagcgt aatggctggc    3840
ctgttgaaca agtctggaaa gaaatgcata agcttttgcc attctcaccg gattcagtcg    3900
tcactcatgg tgatttctca cttgataacc ttattttga cgaggggaaa ttataggtt      3960 gtattgatgt tggacgagtc ggaatcgcag accgatacca ggatcttgcc atcctatgga    4020
actgcctcgg tgagttttct ccttcattac agaaacggct ttttcaaaaa tatggtattg    4080
ataatcctga tatgaataaa ttgcagtttc atttgatgct cgatgagttt ttctaatcag    4140
tactgacaat aaaaagattc ttgttttcaa gaacttgtca tttgtatagt ttttttatat    4200
tgtagttgtt ctattttaat caaatgttag cgtgatttat attttttttc gcctcgacat    4260
catctgccca gatgcgaagt taagtgcgca gaaagtaata tcatgcgtca atcgtatgtg    4320
aatgctggtc gctatactgc tgtcgattcg atactaacgc cgccatccag tacggatcgc    4380
ttgcctgtaa cttacacgcg cctcgtatct tttaatgatg gaataatttg ggaatttact    4440
ctgtgtttat ttatttttat gttttgtatt tggatttag aaagtaaata agaaggtag      4500 aagagttacg gaatgaagaa aaaaaaataa acaaaggttt aaaaaatttc aacaaaaagc    4560
gtactttaca tatatattta ttagacaaga aaagcagatt aaatagatat acattcgatt    4620
aacgataagt aaaatgtaaa atcacaggat tttcgtgtgt ggtcttctac acagacaaga    4680
tgaaacaatt cggcattaat acctgagagc aggaagagca agataaaagg tagtatttgt    4740
tggcgatccc cctagagtct tttacatctt cggaaaacaa aaactatttt ttctttaatt    4800
tcttttttta ctttctattt ttaatttata tatttatatt aaaaaattta aattataatt    4860
atttttatag cacgtgatga aaaggaccca ggtggcactt tcggggaaa tgtgcgcgga    4920 accctatttt gttattttt ctaaatacat tcaaatatgt atccgctcat gagacaataa    4980
ccctgataaa tgcttcaata atattgaaaa aggaagagta tgagtattca acatttccgt    5040
gtcgccctta ttccttttt tgcggcattt tgccttcctg tttttgctca cccagaaacg    5100
ctggtgaaag taaagatgc tgaagatcag ttgggtgcac gagtgggtta catcgaactg    5160
gatctcaaca gcggtaagat ccttgagagt tttcgccccg aagaacgttt tccaatgatg    5220
agcactttta aagttctgct atgtggcgcg gtattatccc gtattgacgc cgggcaagag    5280
caactcggtc gccgcataca ctattctcag aatgacttgg ttgagtactc accagtcaca    5340
```

```
gaaaagcatc ttacggatgg catgacagta agagaattat gcagtgctgc cataaccatg   5400
agtgataaca ctgcggccaa cttacttctg acaacgatcg gaggaccgaa ggagctaacc   5460 gcttttttc  acaacatggg ggatcatgta actcgccttg atcgttggga accggagctg   5520
aatgaagcca taccaaacga cgagcgtgac accacgatgc ctgtagcaat ggcaacaacg   5580
ttgcgcaaac tattaactgg cgaactactt actctagctt cccggcaaca attaatagac   5640
tggatggagg cggataaagt tgcaggacca cttctgcgct cggcccttcc ggctggctgg   5700
tttattgctg ataaatctgg agccggtgag cgtgggtctc gcggtatcat tgcagcactg   5760
gggccagatg gtaagccctc ccgtatcgta gttatctaca cgacgggcag tcaggcaact   5820
atggatgaac gaaatagaca gatcgctgag ataggtgcct cactgattaa gcattggtaa   5880
ctgtcagacc aagtttactc atatatactt tagattgatt taaaacttca ttttaattt    5940 aaaaggatct aggtgaagat cctttttgat aatctcatga ccaaaatccc ttaacgtgag   6000
ttttcgttcc actgagcgtc agaccccgta gaaaagatca aaggatcttc ttgagatcct   6060
ttttttctgc gcgtaatctg ctgcttgcaa acaaaaaaac caccgctacc agcggtggtt   6120
tgtttgccgg atcaagagct accaactctt tttccgaagg taactggctt cagcagagcg   6180
cagataccaa atactgttct tctagtgtag ccgtagttag gccaccactt caagaactct   6240
gtagcaccgc ctacatacct cgctctgcta atcctgttac cagtggctgc tgccagtggc   6300
gataagtcgt gtcttaccgg gttggactca agacgatagt taccggataa ggcgcagcgg   6360
tcgggctgaa cggggggttc gtgcacacag cccagcttgg agcgaacgac ctacaccgaa   6420
ctgagatacc tacagcgtga gctatgagaa agcgccacgc ttcccgaagg gagaaaggcg   6480
gacaggtatc cggtaagcgg cagggtcgga acaggagagc gcacgaggga gcttccaggg   6540
ggaaacgcct ggtatcttta tagtcctgtc gggtttcgcc acctctgact tgagcgtcga   6600
tttttgtgat gctcgtcagg ggggcggagc ctatggaaaa acgccagcaa cgcggccttt   6660
ttacggttcc tggccttttg ctggccttttt gctcacatgt tctttcctgc gttatccct   6720 gattctgtgg ataaccgtat taccgccttt gagtgagctg ataccgctcg ccgcagccga   6780
acgaccgagc gcagcgagtc agtgagcgag gaagcggaag agcgcccaat acgcaaaccg   6840
cctctccccg cgcgttggcc gattcattaa tgcagctggc acgacaggtt cccgactgg    6900 aaagcgggca gtgagcgcaa cgcaattaat gtgagttagc tcactcatta ggcaccccag   6960
gctttacact ttatgcttcc ggctcgtatg ttgtgtggaa ttgtgagcgg ataacaattt   7020
cacacaggaa acagctatga ccatgattac gccaagctcg gaattaaccc tcactaaagg   7080
gaacaaaagc tgggtaccgg gccccccctc gagatccggg atcgaagaaa tgatggtaaa   7140
tgaaatagga aatcaaggag catgaaggca aaagacaaat ataagggtcg aacgaaaaat   7200
aaagtgaaaa gtgttgatat gatgtatttg gctttgcggc gccgaaaaaa cgagtttacg   7260
caattgcaca atcatgctga ctctgtggcg gacccgcgcg cttgccggcc ggcgataac    7320 gctgggcgtg aggctgtgcc cggcggagtt ttttgcgcct gcattttcca aggtttaccc   7380
tgcgctaagg ggcgagattg gagaagcaat aagaatgccg gttggggttg cgatgatgac   7440
gaccacgaca actggtgtca ttatttaagt tgccgaaaga acctgagtgc atttgcaaca   7500
tgagtatact agaagaatga gccaagactt gcgagacgcg agtttgccgg tggtgcgaac   7560
aatagagcga ccatgacctt gaaggtgaga gcgcataac  cgctagagta ctttgaagag   7620
gaaacagcaa tagggttgct accagtataa atagacaggt acatacaaca ctggaaatgg   7680
```

```
ttgtctgttt gagtacgctt tcaattcatt tgggtgtgca ctttattatg ttacaatatg    7740
gaagggaact ttacacttct cctatgcaca tatattaatt aaagtccaat gctagtagag    7800
aaggggggta acacccctcc gcgctctttt ccgatttttt tctaaaccgt ggaatatttc    7860
ggatatcctt tgttgtttc cgggtgtaca atatggactt cctcttttct ggcaaccaaa     7920
cccatacatc gggattccta ataaccttc gttggtctcc ctaacatgta ggtggcggag     7980
gggagatata caatagaaca gataccagac aagacataat gggctaaaca agactacacc    8040
aattacactg cctcattgat ggtggtacat aacgaactaa tactgtagcc ctagacttga    8100
tagccatcat catatcgaag tttcactacc ctttttccat ttgccatcta ttgaagtaat    8160
aataggcgca tgcaacttct tttctttttt tttcttttct ctctcccccg ttgttgtctc    8220
accatatccg caatgacaaa aaatgatgg aagacactaa aggaaaaaat taacgacaaa     8280
gacagcacca acagatgtcg ttgttccaga gctgatgagg ggtatctcga agcacacgaa    8340
acttttcct tccttcattc acgcacacta ctctctaatg agcaacggta tacggccttc     8400
cttccagtta cttgaatttg aaataaaaaa aagtttgctg tcttgctatc aagtataaat    8460
agacctgcaa ttattaatct tttgtttcct cgtcattgtt ctcgttccct ttcttccttg    8520
tttcttttc tgcacaatat ttcaagctat accaagcata caatcaactg agctcatgtc     8580
cacaaaatca taccagta gagctgagac tcatgcaagt ccggttgcat cgaaacttttt    8640
acgtttaatg gatgaaaaga agaccaattt gtgtgcttct cttgacgttc gttcgactga    8700
tgagctattg aaacttgttg aaacgttggg tccatacatt tgccttttga aaacacacgt    8760
tgatatcttg gatgatttca gttatgaggg tactgtcgtt ccattgaaag cattggcaga    8820
gaaatacaag ttcttgatat ttgaggacag aaaattcgcc gatatcggta acacagtcaa    8880
attacaatat acatcgggcg tttaccgtat cgcagaatgg tctgatatca ccaacgccca    8940
cggggttact ggtgctggta ttgttgctgg cttgaaacaa ggtgcgcaag aggtcaccaa    9000
agaaccaagg ggattattga tgcttgctga attgtcttcc aagggttctc tagcacacgg    9060
tgaatatact aagggtaccg ttgatattgc aaagagtgat aaagatttcg ttattgggtt    9120
cattgctcag aacgatatgg gaggaagaga agaagggttt gattggctaa tcatgacccc    9180
aggtgtaggt ttagacgaca aaggcgatgc attgggtcag cagtacagaa ccgtcgacga    9240
agttgtaagt ggtggatcag atatcatcat tgttggcaga ggacttttcg ccaagggtag    9300
agatcctaag gttgaaggtg aaagatacag aaatgctgga tgggaagcgt accaaaagag    9360
aatcagcgct ccccattaat tatacaggaa acttaataga acaaatcaca tatttaatct    9420
aatagccacc tgcattggca cggtgcaaca ctctatggtg cactctcagt acaatctgct    9480
ctgatgccgc atagttaagc caggatccaa tatcaaagga aatgatagca ttgaaggatg    9540
agactaatcc aattgaggag tggcagcata tagaacagct aaagggtagt gctgaaggaa    9600
gcatacgata ccccgcatgg aatgggataa tatcacagga ggtactagac tacctttcat    9660
cctacataaa tagacgcata taagtacgca tttaagcata acacgcact atgccgttct     9720
tctcatgtat atatatatac aggcaacacg cagatatagg tgcgacgtga acagtgagct    9780
gtatgtgcgc agctcgcgtt gcattttcgg aagcgctcgt tttcggaaac gctttgaagt    9840
tcctattccg aagttcctat tctctagcta gaaagtatag gaacttcaga gcgcttttga    9900
aaaccaaaag cgctctgaag acgcactttc aaaaaaccaa aaacgcaccg gactgtaacg    9960
agctactaaa atattgcgaa taccgcttcc acaaacattg ctcaaaagta tctctttgct    10020
atatatctct gtgctatatc cctatataac ctacccatcc acctttcgct ccttgaactt    10080
```

-continued

```
gcatctaaac tcgacctcta cattttttat gtttatctct agtattactc tttagacaaa    10140
aaaattgtag taagaactat tcatagagtg aatcgaaaac aatacgaaaa tgtaaacatt    10200
tcctatacgt agtatataga gacaaaatag aagaaaccgt tcataatttt ctgaccaatg    10260
aagaatcatc aacgctatca ctttctgttc acaaagtatg cgcaatccac atcggtatag    10320
aatataatcg gggatgcctt tatcttgaaa aaatgcaccc gcagcttcgc tagtaatcag    10380
taaacgcggg aagtggagtc aggctttttt tatggaagag aaaatagaca ccaaagtagc    10440
cttcttctaa ccttaacgga cctacagtgc aaaaagttat caagagactg cattatagag    10500
cgcacaaagg agaaaaaaag taatctaaga tgctttgtta gaaaaatagc gctctcggga    10560
tgcatttttg tagaacaaaa aagaagtata gattctttgt tggtaaaata gcgctctcgc    10620
gttgcatttc tgttctgtaa aaatgcagct cagattcttt gtttgaaaaa ttagcgctct    10680
cgcgttgcat ttttgtttta caaaaatgaa gcacagattc ttcgttggta aaatagcgct    10740
ttcgcgttgc atttctgttc tgtaaaaatg cagctcagat tctttgtttg aaaaattagc    10800
gctctcgcgt tgcattttg ttctacaaaa tgaagcacag a                         10841
```

<210> SEQ ID NO 2
<211> LENGTH: 178
<212> TYPE: DNA
<213> ORGANISM: Artificial Sequence
<220> FEATURE:
<223> OTHER INFORMATION: BC30+30
<220> FEATURE:
<221> NAME/KEY: misc_feature
<222> LOCATION: (21)..(50)
<223> OTHER INFORMATION: n is a, c, g, or t
<220> FEATURE:
<221> NAME/KEY: misc_feature
<222> LOCATION: (85)..(94)
<223> OTHER INFORMATION: n is a, c, g, or t
<220> FEATURE:
<221> NAME/KEY: misc_feature
<222> LOCATION: (129)..(158)
<223> OTHER INFORMATION: n is a, c, g, or t

<400> SEQUENCE: 2

```
agcatacaat caactgagct nnnnnnnnnn nnnnnnnnnn nnnnnnnnnn ataacttcgt     60
atagcataca ttatacgaag ttatnnnnnn nnnnataact tcgtatagga tactttatac    120
gaagttatnn nnnnnnnnnn nnnnnnnnnn nnnnnnnnag ctcatgtcca caaaatca      178
```